United States Patent [19]
Lo et al.

[11] Patent Number: 5,876,396
[45] Date of Patent: *Mar. 2, 1999

[54] SYSTEM METHOD AND CONTAINER FOR HOLDING AND DELIVERING A SOLUTION

[75] Inventors: Ying-Cheng Lo, Green Oaks; Marc Bellotti, Libertyville, both of Ill.

[73] Assignee: Baxter International Inc., Deerfield, Ill.

[*] Notice: This patent issued on a continued prosecution application filed under 37 CFR 1.53(d), and is subject to the twenty year patent term provisions of 35 U.S.C. 154(a)(2).

[21] Appl. No.: 722,537

[22] Filed: Sep. 27, 1996

[51] Int. Cl.⁶ .................................................. A61B 19/00
[52] U.S. Cl. .......................... 604/410; 604/408; 604/403; 128/DIG. 24
[58] Field of Search ..................... 604/403, 408, 604/409, 410, 317, 322, 277, 276, 29, 278; 128/DIG. 24

[56] References Cited

U.S. PATENT DOCUMENTS

| | | |
|---|---|---|
| 3,554,256 | 1/1971 | Anderson . |
| 4,411,358 | 10/1983 | Benuwiki et al. ............... 206/45.34 |
| 4,432,763 | 2/1984 | Manschat et al. ............... 604/262 |
| 4,608,043 | 8/1986 | Larking ............................ 604/87 |
| 4,619,650 | 10/1986 | Wisdom ........................... 604/408 |
| 4,863,452 | 9/1989 | Irmiter et al. .................... 604/408 |
| 5,211,643 | 5/1993 | Reinhardt et al. ............... 604/416 |
| 5,257,985 | 11/1993 | Puhl ................................. 604/410 |
| 5,509,898 | 4/1996 | Isono et al. ...................... 604/87 |

FOREIGN PATENT DOCUMENTS

| | | |
|---|---|---|
| 8302061 | 6/1983 | WIPO . |
| 9639207 | 12/1996 | WIPO . |

*Primary Examiner*—Corrine M. McDermott
*Assistant Examiner*—Cris L. Rodriguez
*Attorney, Agent, or Firm*—Thomas S. Borecki; Charles R. Mattenson; Robert M. Barrett

[57] ABSTRACT

A system and a method for administering a solution (12) from a container (10) to a patient (35) are provided. The container (10) is divided into a solution side (16) and a drain side (18) separated by a tear line (20). The solution side (16) and the drain side (18) are in fluid communication with one another and with a port (28) that connects to the patient (35). The container (10) is separable at the tear line (20) such that contents of a peritoneum cavity of the patient (35) may be drained into the drain side (18) of the container (10). Then, the solution (12) from the solution side (16) of the container (10) may be drained from the container (10) into the patient (35).

14 Claims, 3 Drawing Sheets

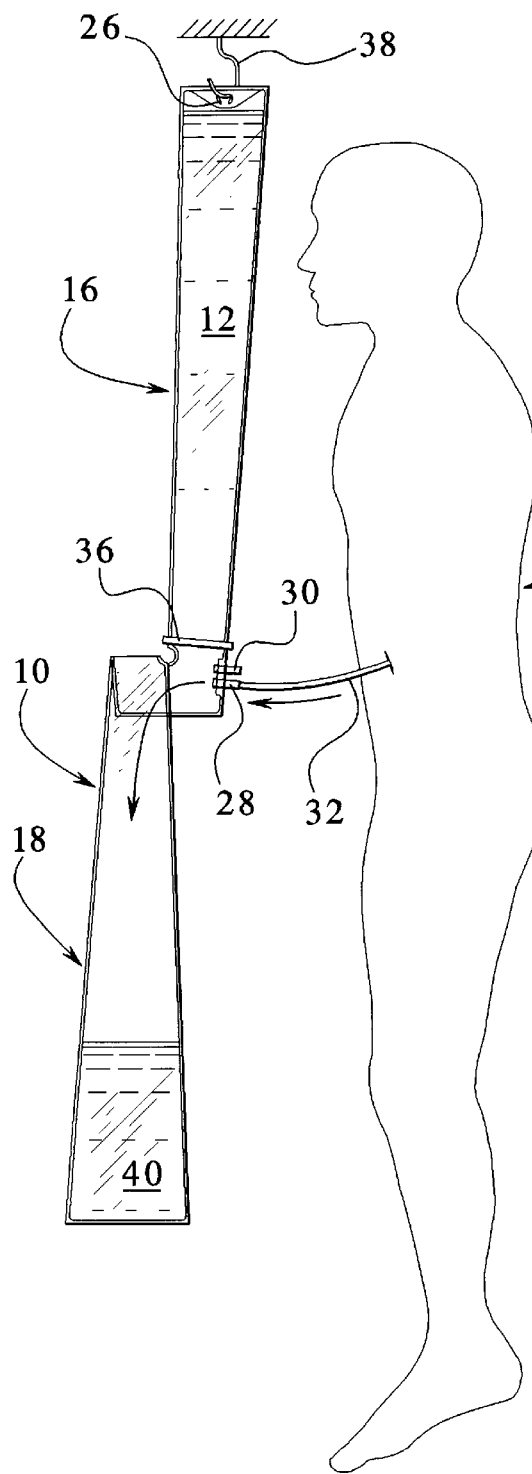
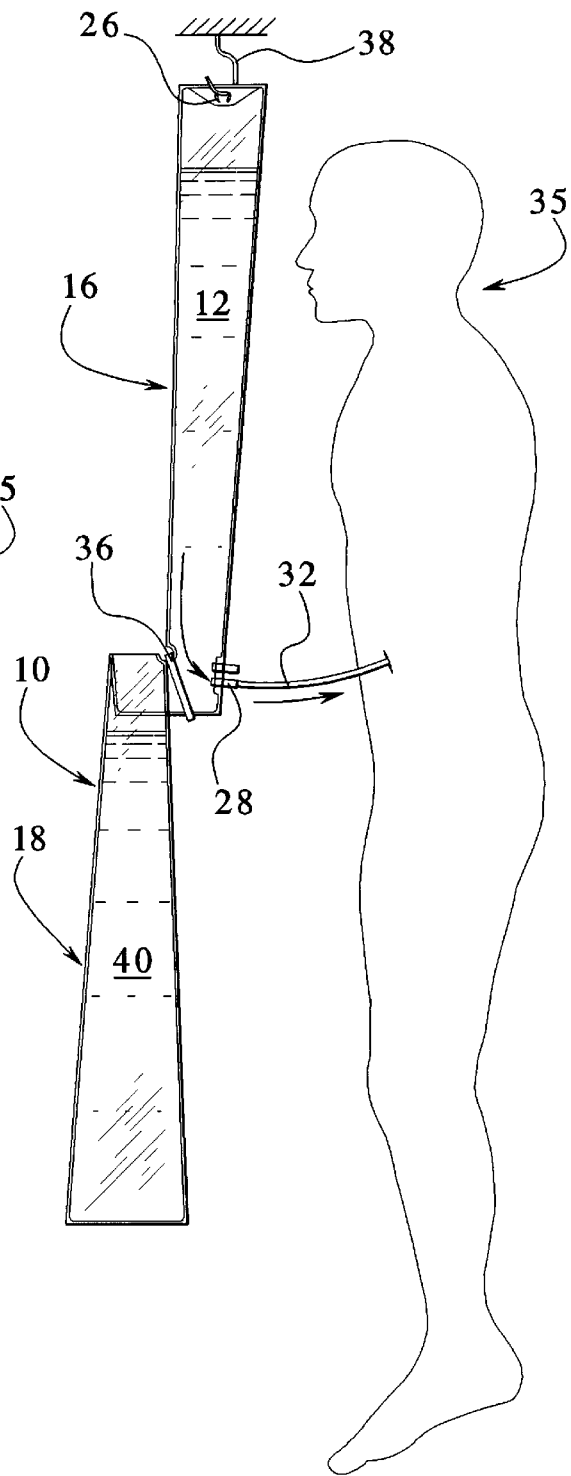

SYSTEM METHOD AND CONTAINER FOR HOLDING AND DELIVERING A SOLUTION

BACKGROUND OF THE INVENTION

The present invention generally relates to a system, a method and a container for holding and dispensing a solution. More specifically, the present invention relates to a system, a method and a container for delivering a solution to a patient undergoing peritoneal dialysis as well as draining a peritoneum of the patient.

It is, of course, known to administer solutions to patients. One such procedure that requires delivery of a solution to a patient is for a patient undergoing peritoneal dialysis.

In a known procedure for continuous ambulatory peritoneal dialysis (CAPD), two containers are required to perform the procedure. A first container, or drain bag, is provided along with a length of tubing that is connectable to the peritoneum of a patient for draining the peritoneum. A second container, or solution container, includes a dialysate therein for feeding to a patient. After the peritoneum fluid is drained into the drain bag, the solution bag is connected to the patient. The dialysate is delivered via the tubing from the solution bag to the peritoneum of the patient.

The use of two bags to perform CAPD, however, requires a number of additional steps. For example, prior to delivering the dialysate to the patient, the tubing connected to the solution bag must be primed in order to remove any air from the tubing. In addition, frangibles are often provided or required in the lengths of the tubing or connectors connected to the tubing. Selective fluid communication is initiated by breaking of the frangible thereby allowing dialysate to flow from the solution bag into the peritoneum of the patient.

As is clearly evident from the foregoing, the known procedure is complex in that a number of components and additional steps are often required to perform the procedure. More specifically, at least a solution bag, a drain bag, tubing extending from each of the bags, connectors, at least one frangible, and caps on the connectors are required to perform CAPD using a two bag system.

A need, therefore, exists for an improved system, method and container that overcomes the deficiencies of known systems and procedures for administering solutions and simplifies the known procedures and systems.

SUMMARY OF THE INVENTION

A system, a method and a container are provided for administering a solution. The container holds the solution for delivery, for example, to a patient undergoing peritoneal dialysis, and also is capable of receiving solution separately from the area in which the solution is held.

In an embodiment of the present invention, a system is provided for holding and administering a solution. The system has a container having walls defining an interior holding the solution therein wherein the container is divided into two chambers in fluid communication therewith and further wherein the two chambers are substantially parallel to each other and are of substantially equal length. A separation line is formed between the two chambers along substantially the length of each of the two chambers.

In an embodiment, a port is provided which is in fluid communication with the two chambers.

In an embodiment, an aperture is provided at one end of one of the two chambers to suspend the chamber.

In an embodiment, the lengths of the two chambers are substantially greater than the widths.

In an embodiment, a medication port is provided in fluid communication with the two chambers.

In an embodiment, volume of one of the two chambers is greater than volume of the other one of the two chambers.

In an embodiment, volume of one of the two chambers is at least 1.5 times greater than volume of the other one of the two chambers.

In an embodiment, the solution may be delivered to the patient without additional tubing.

In another embodiment of the present invention, a method of delivering a solution to a patient is provided. The method comprises the steps of: providing a container having an interior holding a solution wherein the container is divisible into two chambers; providing a port in fluid communication with each of the two chambers; sealing a portion of the container to separate the solution into only one of the two chambers; and connecting the port to the patient to provide fluid communication with the patient.

In an embodiment, the method further comprises the step of connecting a length of tubing between the port and the patient.

In an embodiment, a medication port is provided in fluid communication with the two chambers.

In an embodiment, the method further comprises the step of suspending one of the two chambers through an aperture at one end of the chamber.

In an embodiment, the method further comprises the step of separating the two chambers along a length of the two chambers such that one chamber is substantially sealed from the other chamber.

In an embodiment, the method further comprises the step of separating the two chambers along a line of separation extending substantially along a length between the two chambers wherein the line of separation may be selectively broken to separate the two chambers along the line of separation.

In an embodiment, one of the two chambers has a volume greater than the other one of the two chambers.

In another embodiment of the present invention, a container is provided having a first chamber having an interior capable of holding a solution therein. A second chamber has an interior capable of holding a solution wherein the second chamber is in selective communication with and integrally formed with the first chamber. A port is in selective communication with the first chamber or the second chamber.

In an embodiment, an aperture is provided in only one of the first chamber or the second chamber.

In an embodiment, a line of separation is provided between the first chamber and the second chamber dividing the first chamber and the second chamber along a length running between the first chamber and the second chamber. The length is substantially equal to, but not greater than, an entire length of either the first chamber or the second chamber.

In an embodiment, volume of the first chamber is greater than volume of the second chamber.

In an embodiment, lengths of the first chamber and the second chamber are substantially equal, and volume of the first chamber is greater than volume of the second chamber.

In an embodiment, a line of separation is provided between the first chamber and the second chamber selectively separable to divide the first chamber from the second chamber and maintain fluid communication between the first chamber and the second chamber.

It is, therefore, an advantage of the present invention to provide a system, a method and a container for simplifying administration of a solution to a patient.

Another advantage of the present invention is to provide a system, a method, and a container for administering a solution to a patient that is simple to manufacture.

Yet another advantage of the present invention is to provide a system, a method and a container that may be used as both the solution bag and the drain bag.

And, another advantage of the present invention is to provide a system, a method and a container that administers solution to a patient without requiring additional tubing.

Moreover, an advantage of the present invention is to provide a system, a method and a container that is easily separable between two separate chambers prior to use.

A still further advantage of the present invention is to provide a system, a method and a container that administers solution to a patient without priming of tubing.

Yet another advantage of the present invention is to provide a system, a method and a container in which sticking of film materials is eliminated during sterilization.

And, another advantage of the present invention is to provide a system, a method and a container that requires shorter sterilization times with more uniform temperatures distribution in the bag.

These and other advantages of the present invention are described in, and will be apparent from, the detailed description of the presently preferred embodiments and from the drawings.

BRIEF DESCRIPTION OF THE DRAWINGS

FIG. 2 illustrates a plan view of an embodiment of the system of the present invention illustrated in FIG. 1 during a draining phase.

FIG. 3 illustrates a plan view of an embodiment of the system of the present invention illustrated in FIG. 1 during a stage in which solution is administered to a patient from a container.

DETAILED DESCRIPTION OF THE PRESENTLY PREFERRED EMBODIMENTS

The present invention provides a system, a method and a container for holding and delivering a solution. The container used in the system and method of the present invention is multi-chambered having interiors holding a solution. The solution may be manipulated from one chamber to another during use of the system to perform the method of the present invention.

Figure 1:
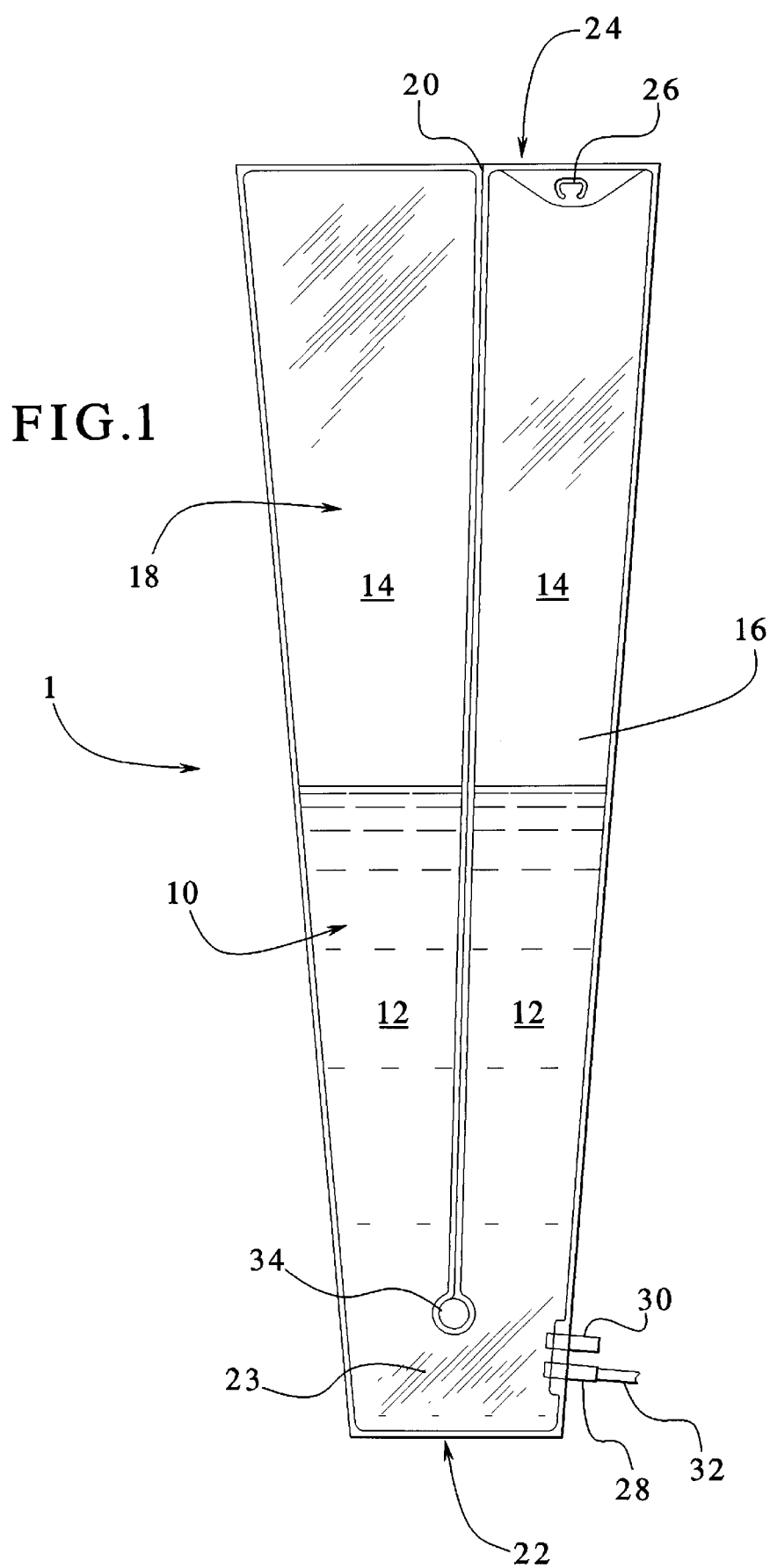
FIG. 1 illustrates a plan view of an embodiment of a system of the present invention for holding and administering a solution.

Referring now to the drawings wherein like numerals refer to like parts, FIG. 1 illustrates a system 1 including a container 10 having a solution 12 within an interior 14 of the container 10. The container 10 is divided into a solution side 16 and a drain side 18 separated by a tear line 20. The solution side 16 and the drain side 18 are in fluid communication at an end 22 of the container 10 through a channel 23 such that the solution 12 within the container 10 may be isolated on either the solution side 16 or the drain side 18. At an opposite end 24 of the container 10 on the solution side 16 is an aperture 26 whose function will be described with reference to FIGS. 2 and 3.

In fluid communication with the container 10 is a port 28. Also provided is an optional medication port 30 used to provide medication to the interior 14 of the container 10, if necessary. In operation, the port 28 may be connected to a length of tubing 32. Alternatively, the port 28 may be connected directly to a device connected to a patient that provides fluid communication with, for example, a peritoneum cavity of the patient.

As illustrated, the drain side 18 of the container 10 is larger in volume than the solution side 16. In a preferred embodiment, the drain side 18 has a volume at least 1.5 times greater than the solution side 16. The walls of both the solution side 16 and the drain side 18 are preferably tapered as illustrated in FIG. 1. The channel 23 formed at the end 22 of the container 10 allows the solution 12 to freely flow from either the solution side 16 or the drain side 18 of the container 10. The channel 23 is formed between a terminating end 34 of the tear line 20 and the end 22 of the container 10. During manufacture of the container 10, the tear line 20 is formed by a sealing technique well-known by those skilled in the art. The tear line 20 is formed substantially simultaneously with the formation of the walls of the container 10.

Referring now to FIGS. 2 and 3, use of the container 10 by a patient 35 is illustrated. To begin operation, the solution 12 within the container 10 is first transferred to the solution side 16 of the container 10. Therefore, prior to draining of the peritoneum cavity of the patient 35, the drain side 18 is substantially empty through isolation of the solution 12 on the solution side 16 of the container 10. After transferring the solution 12 to the solution side 16, a clamp 36 is placed at a point to separate the port 28 from the solution 12. Either prior to clamping or prior to draining of the peritoneum of the patient 35, the tear line 20 is torn to separate the solution side 16 from the drain side 18. The solution side 16 may be suspended by a hook or other known means through the aperture 26 at the end of the drain side 18 of the container 10 as illustrated. The peritoneum of the patient 35 is then drained into the drain side 18 of the container 10.

After draining the peritoneum or substantially after completion of the same, the clamp 36 may be moved to the position illustrated in FIG. 3. Preferably, a second clamp is placed in the position illustrated in FIG. 3 and then the clamp 36 illustrated in the position in FIG. 2 is removed from the solution side 16. At this stage, the drain side 18 is at least partially filled with drainage from the peritoneum cavity of the patient 35 as generally designated by 40 in FIGS. 2 and 3.

Then, the solution 12 in the solution side 16 of the container 10 may be drained through the port 28 into the peritoneum cavity of the patient 35. A tubing 32 is illustrated connected between the port 28 and the peritoneum cavity of the patient 35. However, the port 28 may be directly connected to a connecting device (not shown) that, in turn, is connected to the peritoneum cavity. After the solution 12 is drained from the solution side 16 into the peritoneum cavity of the patient 35, the container 10 may be disconnected from the patient 35.

Figure 4:
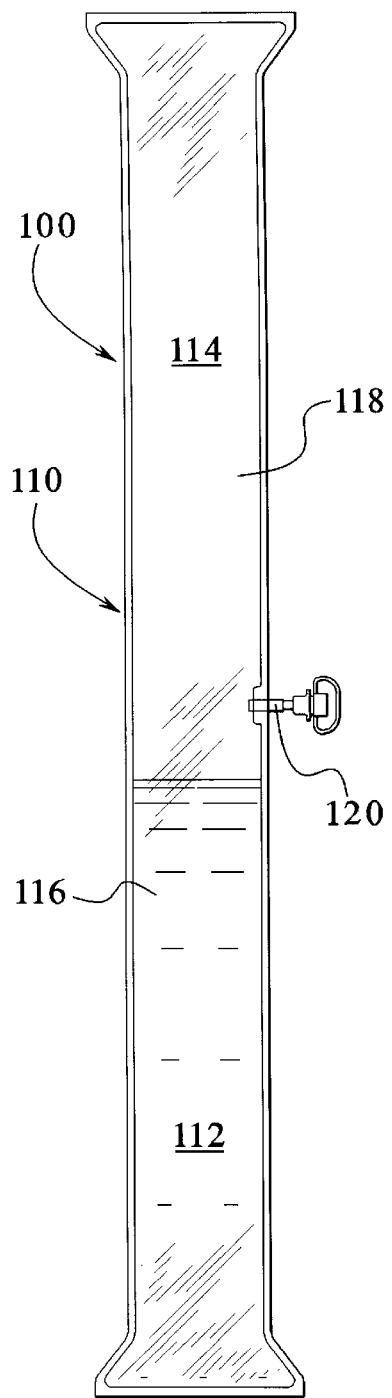
FIG. 4 illustrates a plan view of an alternate embodiment of a system of the present invention for holding and administering a solution to a patient.
Figure 5:
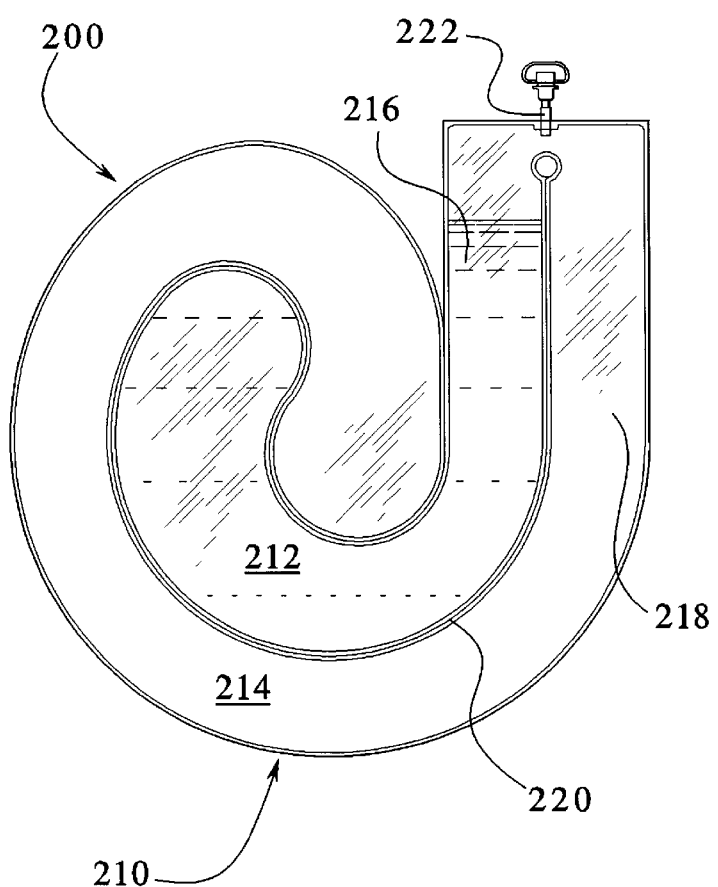
FIG. 5 illustrates a plan view of yet another embodiment of a system of the present invention for holding and administering a solution to a patient.

Referring now to FIGS. 4 and 5, alternate embodiments of the system illustrated in FIG. 1 are illustrated. As shown in FIG. 4, a system 100 includes a container 110 having a solution 112 located within the interior 114 of the container 110. The container 110 can be obtained from blown film process. The interior of the container 110 is divided into a solution side 116 and a drain side 118. A clamp or clamps (not shown) may be placed across a width of the container 110 in positions that maintain the solution 112 on the solution side 116 during draining of the peritoneum cavity into the drain side 118 through a port 120. After draining, a second clamp may be placed across a width of the container 110 to maintain the drainage from the peritoneum cavity on the drain side 118. Then, the first clamp may be removed to allow draining of the solution 112 from the solution side 116 into the peritoneum cavity. Although not shown, the container 110 may include an aperture on the solution side 116 such that the system 100 may be suspended similar to the manner illustrated in FIGS. 2 and 3.

Referring now to FIG. 5, another alternate embodiment of a system 200 is illustrated with a container 210 having a solution 212 within an interior 214 of the container 210. Again, the container 210 includes a solution side 216 and a drain side 218. The solution side 216 and the drain side 218 are divided by a tear line 220. To use the system 200, the solution side 216 and the drain side 218 are separated at the tear line 220. A clamp (not shown) may be placed at a point across a width of the solution side 216 to maintain or isolate the solution 212 on the solution side 216 and to prevent fluid communication of the solution 212 through a port 222. A peritoneum cavity of a patient may then be drained through the port 222 into the drain side 218 of the container 210. A second clamp may then be placed at a point across a width of the drain side 218 to prevent fluid communication of the drainage from the patient between the drain side 218 and the port 222. The first clamp may then be removed, and the solution side 216 may be drained of the solution 212 from the solution side 216 of the container 210 into the peritoneum cavity of the patient.

Although the present invention has been described with reference to a system and a method for use in peritoneal dialysis, it should be understood that the present invention may be implemented in other processes, such as, but not limited to, intravenous feeding. In addition, although the present invention, as illustrated, shows containers may from a flexible material, such as polyvinyl chloride (PVC), other materials may be implemented by those skilled in the art, such as non-PVC materials.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

We claim:

1. A system for holding and administering a solution, the system comprising:
    a container having walls defining an interior holding the solution therein wherein the container includes two chambers in fluid communication with each other and further wherein the two chambers are connected to each other at base ends of each chamber and the two chambers are of substantially equal length defined between the base ends of the two chambers and top ends of the two chambers;
    the two chambers being detachably connected by a vertical tear line formed between the two chambers along substantially a length of each of the chambers wherein the tear line begins at and extends through the top ends of the two chambers and extends toward the base ends of the two chambers wherein the two chambers are selectively separable along the tear line so that one chamber will hang below the other chamber when the other chamber is suspended by its top end; and
    a port in fluid communication with the two chambers wherein the port is provided near the base end of one of the two chambers.

2. The system of claim 1 further comprising:
    an aperture at one end of one of the two chambers to suspend the chamber.

3. The system of claim 1 wherein the lengths of the two chambers are substantially greater than the widths.

4. The system of claim 1 further comprising:
    a medication port in fluid communication with the two chambers.

5. The system of claim 1 wherein volume of one of the two chambers is greater than volume of the other of the two chambers.

6. The system of claim 1 wherein volume of one of the two chambers is at least 1.5 times greater than volume of the other of the two chambers.

7. The system of claim 1 wherein the solution may be delivered to the patient without additional tubing.

8. A container comprising:
    a first chamber having an interior capable of holding a solution therein;
    a second chamber having an interior capable of holding a solution wherein the second chamber is in selective communication with and integrally formed with the first chamber defining a length of each of the chambers between a first end and a second end;
    a port in selective communication with the first chamber or the second chamber wherein the port is located near the second end of the chambers; and
    a line of separation between the first chamber and the second chamber dividing the first chamber and the second chamber along a separable length running between the first chamber and the second chamber wherein the separable length begins at the first end of the separable length and ends at the second end and further wherein the chambers are separable along the line of separation.

9. The container of claim 8 further comprising:
    an aperture through an end of only one of the first chamber or the second chamber.

10. The container of claim 8 wherein the separable length is substantially equal to, but not greater than, an entire length of either the first chamber or the second chamber.

11. The container of claim 8 wherein volume of the first chamber is greater than volume of the second chamber.

12. The container of claim 8 wherein lengths of the first chamber and the second chamber are substantially equal and volume of the first chamber is greater than volume of the second chamber.

13. The container of claim 8 wherein the line of separation between the first chamber and the second chamber is selectively separable to divide the first chamber from the second chamber and maintain fluid communication between the first chamber and the second chamber.

14. A system for holding and administering a solution, the system comprising:
    a container having walls defining an interior holding the solution therein wherein the container is divided into two chambers in fluid communication therewith and further wherein the two chambers are substantially parallel to each other and are of substantially equal length defined between a base end and a top end of the container;

a separation line formed between the two chambers along substantially a length of each of the two chambers wherein the separation line begins at the top end of the container and extends toward the base end of the container wherein the chambers are selectively separable along the separation line;

a port in fluid communication with the two chambers wherein the port is provided near the base end of one of the two chambers; and an aperture at one end of one of the two chambers to suspend the chamber.

* * * * *